United States Patent [19]

Banko

[11] 3,937,222

[45] Feb. 10, 1976

[54] SURGICAL INSTRUMENT EMPLOYING CUTTER MEANS

[75] Inventor: Anton Banko, Bronx, N.Y.

[73] Assignee: Surgical Design Corporation, Long Island City, N.Y.

[22] Filed: Nov. 9, 1973

[21] Appl. No.: 414,221

[52] U.S. Cl. ............................................ 128/305
[51] Int. Cl.² .................................... A61B 17/32
[58] Field of Search ........................... 128/305, 312

[56] References Cited
UNITED STATES PATENTS

| | | | |
|---|---|---|---|
| 3,384,085 | 5/1968 | Hall | 128/305 |
| 3,614,953 | 10/1971 | Moss | 128/305 |
| 3,618,611 | 11/1971 | Urban | 128/305 |
| 3,732,858 | 5/1973 | Banko | 128/305 |
| 3,736,938 | 6/1973 | Evvard et al | 128/305 |
| 3,809,093 | 5/1974 | Abraham | 128/305 |

FOREIGN PATENTS OR APPLICATIONS

| | | | |
|---|---|---|---|
| 326,852 | 3/1930 | United Kingdom | 128/305 |

OTHER PUBLICATIONS

Douvas Nicholas G., "The Cataract Roto–Extractor", Amer. Acad. of Ophthal. and Otolaryng., 77: OP-79-2-OP-800. 1973.

*Primary Examiner*—Channing L. Pace
*Attorney, Agent, or Firm*—Darby & Darby

[57] ABSTRACT

A surgical instrument including a cutter for removing objects from the body of a human or animal in vivo, such as the lens in the eye, in which a rotatable cutter is used having a shield through which irrigation fluid is applied to the eye and also through which material severed from the object can be removed. In a preferred embodiment of the invention, a spiral groove is formed as part of the cutter to produce an evacuation of removed material alone or in a suspension. The cutter also has a burr which is coated with an efficient cutting material such as diamond dust and can also include a coating of a non-sticking lubricant.

20 Claims, 21 Drawing Figures

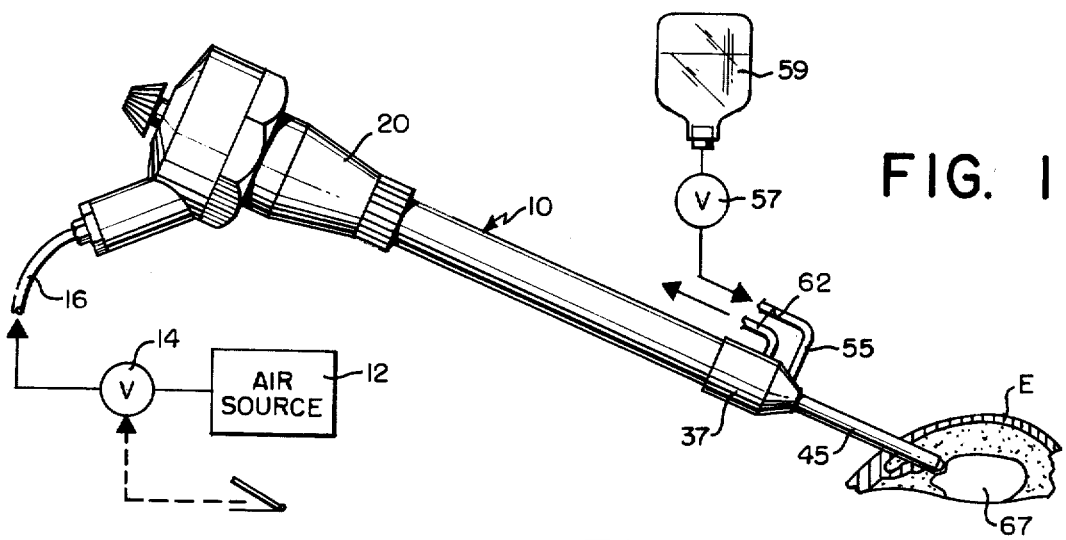
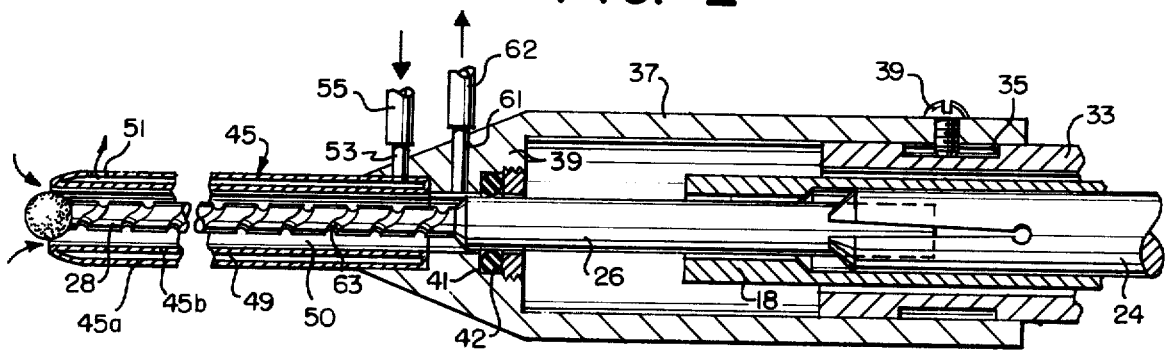
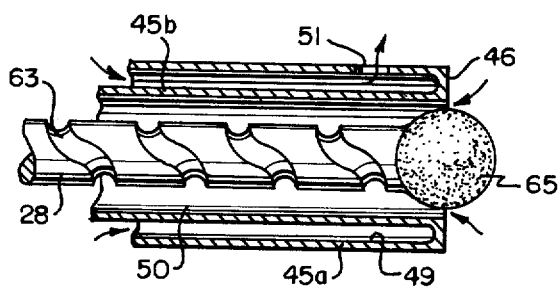
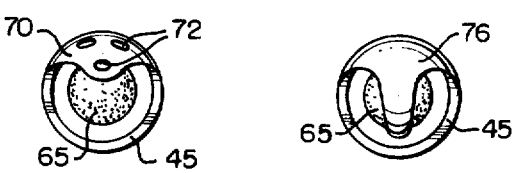
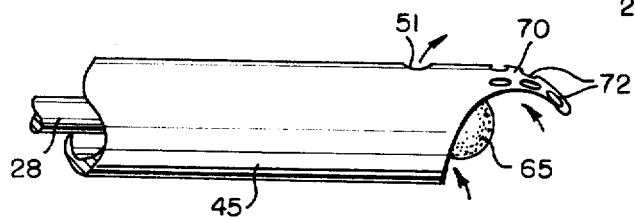
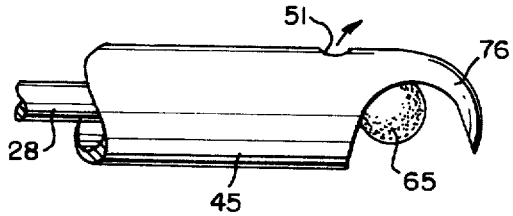

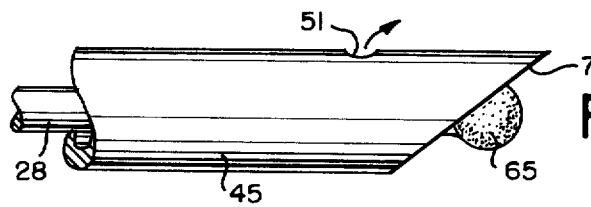 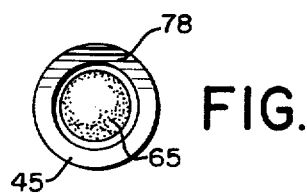
FIG. 6A        FIG. 6B
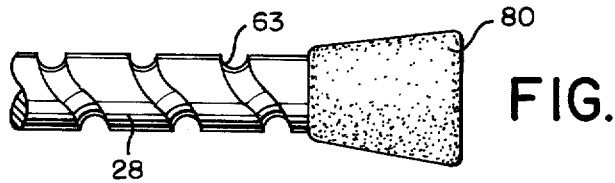 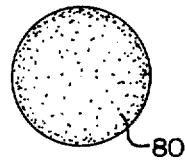
FIG. 7A        FIG. 7B
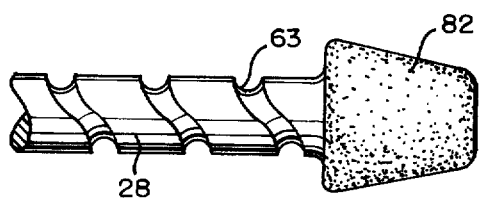 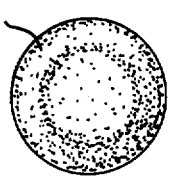
FIG. 8A        FIG. 8B
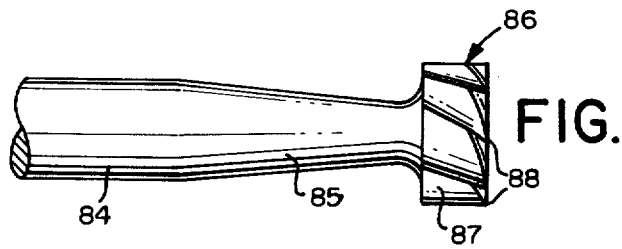 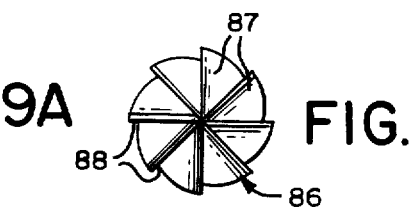
FIG. 9A        FIG. 9B
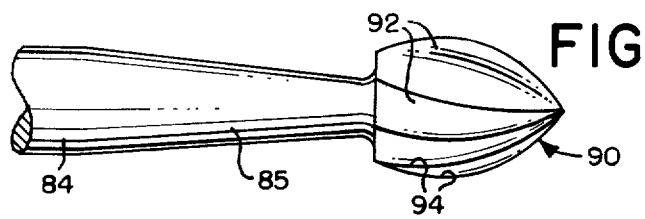 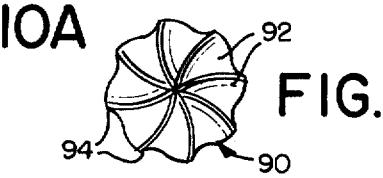
FIG. 10A       FIG. 10B
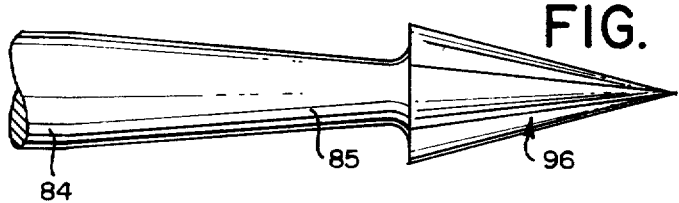 
FIG. 11A       FIG. 11B
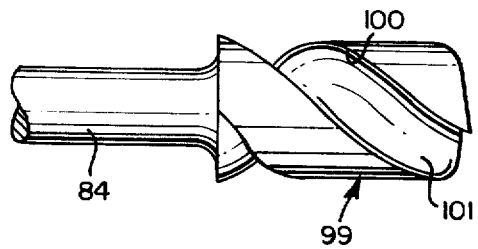 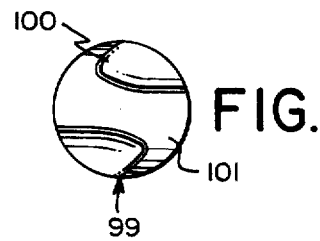
FIG. 12A       FIG. 12B

SURGICAL INSTRUMENT EMPLOYING CUTTER MEANS

Certain surgical applications exist wherein objects are to be removed from the body of a human or animal in vivo. As a typical case, an incision is made in the body and a surgical instrument is inserted through the incision to remove the material. One application of this type exists in the removal of lenses from the eye which have become diseased, so-called cataracts. Various instruments have been used for this particular application of material removal, some of which are shown in my U.S. Patent application Ser. No. 263,448, filed June 16, 1972 and my U.S. Pat. No. 3,732,858, issued May 15, 1973.

In some cases where the object is relatively hard, such as a cataract in an advanced stage, varying techniques must be utilized to try to remove it, depending upon the particular situation. Typical of these techniques are the use of ultrasonic energy which is applied by a probe to the object or a mechanical cutting action. In some cases, the ultrasonic energy cannot efficiently remove material from a relatively hard object. A similar difficulty exists with certain types of mechanical cutters.

The present invention relates to surgical instruments of the mechanical cutting type for removing objects of relatively hard material, such as cataracts, through an incision made in the body of a human or animal. In accordance with the invention, a high-speed rotatable drill is utilized having a cutter at the end thereof. The drill is covered by a protective shield including two concentric members through which fluid is applied to irrigate the eye and also through which the material cut from the object can be removed. The shield is preferably made movable longitudinally of the axis of the instrument so that the exposure of the operative portion of the cutter can be changed to control the cutting action. In a preferred embodiment of the invention, the cutting surface is coated with an effective cutting agent, such as diamond dust.

In a preferred embodiment of the invention, the cutter has a fluted helical groove to assist in drawing material into active cutting relationship with the cutter and in the evacuation of the removed material out through the outlet passage of the instrument.

It is therefore an object of the present invention to provide surgical instruments for removal of objects or tissue from the body in vivo.

It is still a further object of the invention to provide a surgical cutting instrument for removal of objects including a shield for covering the cutter.

Another object is to provide a surgical instrument in which a cutter having an active end is covered by a shield which is movable longitudinally of the instrument to cover selected portions of the cutter.

Yet a further object is to provide a surgical instrument having a cutter whose active surface portion is coated with a cutting agent such as diamond dust.

Other objects and advantages of the present invention will become more apparent upon reference to the following specification and annexed drawings, in which:

FIG. 1 is a plan view of the instrument as part of a complete system;

FIG. 2 is a cross-sectional view of the instrument;

FIG. 3 is a view partly in cross-section showing one embodiment of drill and shield in accordance with the invention;

FIGS. 4A and 4B are side elevational and front views respectively of another embodiment of the shield;

FIGS. 5A and 5B are side elevational and front views respectively of still a further embodiment of the shield;

FIGS. 6A and 6B are side and front views of still a further embodiment of the shield; and FIGS. 7A and 7B through FIGS. 12A–12B are sets of side and front views, each set depicting a portion of another embodiment of instrument.

Referring to FIGS. 1 and 2, the instrument 10 of the subject application is illustratively shown as a turbine type device operated from a source of energy, such as an air source 12, controlled through a foot switch 14. It should be understood, of course, that the instrument can be operated by an electric motor or other suitable energy source. The air from the source 12 passes through a conduit 16 to the instrument 10 where it reacts with turbine blades (not shown) to cause rotation of a shaft 18 held within the instrument housing 20. Shaft 18 includes a chuck 24 for holding the shaft 26 of a cutter 28. Rotation of the turbine shaft 18 relative to chuck 24 bring the two together to lock the drill in place by well known means (not shown).

The end of the turbine shaft 18 associated with chuck 24 is located within a portion 33 of the instrument housing having a grooved surface 35 partially or completely therearound. A cap 37 closes off the end of the instrument and shaft 18. One end of the cap includes a threaded set screw 39 adapted to hold the cap 37 to the housing portion 33 with the cap being rotatable and also adjustable longitudinally of the axis of the instrument by moving it with respect to the groove 35.

The end of the cap 37 narrows down at 39 and is formed with an inner cylindrical groove 41 in which is housed an O-ring 42. The cutter shaft 26 rotates within the O-ring 42 in a central opening in the end 39.

A shield 45 is fastened to the narrow end 39 of cap 37. Shield 45 has concentric outer and inner walls 45a and 45b defining a passage 49 therebetween. An opening 51 is provided in the shield 45 near its end remote from cap 37 and a fluid coupling 53 is attached to the end 39 of the cap to communicate with passage 49. A flexible tubing 55 is attached to coupling 53 and communicates with a valve 57 to a fluid supply source 59, illustratively shown as a bottle. A second fluid coupling 61 is located in the end 39 of the cap to communicate with the passage 50 defined by the interior shield wall 45b, that is, around cutter 28. A tubing 62 is connected to coupling 61 to provide an evacuation outflow in passage 50. This can be provided, for example, by a syringe type device or a powered suction source. In the latter case, the suction rate is preferably made controllable.

FIG. 3 shows one form of cutter 28 for use with the instrument and its relationship to shield 45. This cutter includes a spiral flute 63 cut into its body along the length located within the shield 45 and a spherical ball, or burr, 65 at its end. In FIG. 3, a flat end 46 of shield 45 closes off passage 49 and the external surface of the end is generally cylindrical in shape. The cutter 28, including the burr 65, can be made from a single piece of material, for example, high grade, heat treated stainless steel. The burr 65 is then coated with an effective abrasive material, such as diamond dust. In a typical example, burr 65 can be approximately 1 mm in diameter. Of course, other dimensions can be utilized. If desired, the burr 65 also can be coated with a stick resistant agent such as, for example, TEFLON. This prevents the material removed from the object from sticking to the burr.

The operation of the instrument is described with respect to FIGS. 1–3. There, the shield 45 is shown passing through an incision made in an eye E so that the burr 65 of the cutter 28 is adjacent a lens 67 which is to be removed from within the eye. Air is supplied to the turbine causing the cutter 28 to rotate. Upon rotation, the spiral flute 63 on the body of the cutter produces a suction type action which causes the lens to be drawn towards the burr 65. Suction pressure applied through passage 50 also can be used to assist in drawing the object toward burr 65. The longitudinal position of the shield 45 can be changed to control the amount of burr 65 that is exposed. This provides a safety feature to reduce the exposure of burr 65 to those parts of the object (tissue) or surrounding area which is not to be cut.

Irrigation fluid is supplied to the eye through passage 49 and exits from opening 51. This aids in maintaining the pressure within the operating area, here the eye capsule. The material from the lens is cut, or ground, off. Suction pressure can be applied through the shield central passage 50 to aid in the removal of the material.

FIGS. 4A and 4B show a modification of the shield 45. Here, the front end of the shield is cut away to provide a hood 70. The hood 70 has a number of openings 72. The purpose of these openings is to hold a small piece of an object being cut between the burr 65 and the inner surface of the hood so that it will not rotate. That is, as the piece of the object being cut is drawn into the passageway into relationship with the burr 65, portions of it will extend through the holes 72 and be held therein where it can be cut. As explained previously, the shield can be moved longitudinally. Therefore, the burr 65 can be moved close to the hood 70. A similar result achieved by the use of openings 72 can be obtained, for example, by making the holes 72 with sharp projections around the inner surface thereof, for example like a food grater, or by providing another abrasive surface on the inner surface of the hood. In FIGS. 4A–4B, the end of hood 70 extends down to slightly above the longitudinal axis of drill 28 and the center of burr 65. As before, the longitudinal position of the sleeve can be adjusted.

FIGS. 5A and 5B show a further type of shield 45 in which a hood 76 is also used. In this case, the end 78 of the hood 76 extends down to completely cover the burr 65. The sides of hood 76 are cut away so that the burr is exposed from both sides. This makes the instrument suitable for a side cutting function.

FIGS. 6A and 6B show a still further embodiment of the shield in which the front end 78 is cut at an angle to the longitudinal axis of the shield. Here a variety of exposures are available for the burr 65 depending upon the position of shield 45.

FIGS. 7A and 7B show a further type of cutter 28 which can be used with any one of the shields shown in FIGS. 3 through 6. Here, the burr 80 is shaped as an inverted truncated cone with the large diameter loose end being exposed. Again, this cutter can be made from one piece and the burr 80 coated with diamond dust or other suitable abrasive material.

In FIGS. 8A and 8B, the burr 82 is a truncated cone which is fastened to the end of the cutter 28 at its larger diameter base portion. This is the opposite arrangement from that shown in FIGS. 7A and 7B. Again, the burr is covered with diamond dust, or other suitable abrasive material, and can also be covered with the non-stick material.

FIGS. 9A and 9B show another embodiment of cutter. Here, the cutter has a shaft 84 which is not fluted and which tapers down at 85. The active end 86 has a plurality of blades 87 and is attached to section 85 of the shaft. The leading points 88 of the blades 87 extend outwardly so that when the forward end of the cutter 86 is placed against an object, the points 88 perform a chopping action. While eight blades are shown for the cutter 86, it should be understood that any number of blades can be utilized. The cutter of FIGS. 9A and 9B can also be used with any of the shields of FIGS. 3–6.

FIGS. 10A and 10B show still a further embodiment of cutter 90 which is a paraboloid shaped object having a number of blades 92 formed thereon. The leading edges 94 of the blades are exposed to perform the cutting action and either the tapered front end of the cutter or the wider side can be used to perform the cutting action, depending upon the exposure.

In FIGS. 11A and 11B, the cutter 96 is conical in shape with a number of blade edges 97 formed.

In FIGS. 12A and 12B, a cutter 99 is utilized having blade edges 100 formed on each side of a flute 101. The front surface of the blades 101 is active so that either front cutting or side cutting can be accomplished.

The cutters of FIGS. 9–12 are each capable of producing some action drawing the object to be cut toward the end of the shield also some action to aid in the evacuation of the cut material depending upon the shape of the blades and their direction of rotation. Cutter 99 of FIG. 12 corresponds to cutter 28 of FIGS. 3–8 since it has the flute 101.

In each of the embodiments of FIGS. 9 through 12, the cutter at the respective end of the shaft is not shown coated with the abrasive cutting or non-stick agents, although it could be. The materials for the instruments of FIGS. 9 through 12 can also comprise high-grade, heat-treated, stainless steel. Here again, in each of FIGS. 9–12, any one of the shields of FIGS. 3–6 can be utilized and the longitudinal position of these shields can be adjusted with respect to the cutter to determine the active cutting surface. Further, a spiral groove can be formed along the reduced diameter lengths of the various cutters to assist the action of drawing the material toward the shield and evacuating the cut material.

While the term cutter is used herein, it should be understood that the action produced may actually be more of a grinding type depending upon the circumstances.

What is claimed is:

1. A surgical instrument for abrasively removing at least a part of a body organ comprising a shaft having abrasive cutting means at one end thereof, means for rotating said shaft, tubular means surrounding a portion of said shaft and having an end portion for shielding a portion of said abrasive cutting means while leaving a portion thereof exposed to engage the organ, means for adjusting the position of said tubular means longitudinally of the instrument shaft to control the amount of exposure of the abrasive cutting means with respect to the organ and the space surrounding the organ, said abrasive cutting means being spaced from said tubular means, and means communicating with the interior of said tubular means to remove material which is separated from the organ by said abrasive cutting means.

2. A surgical instrument as in claim 1 wherein said tubular means includes passage means formed in the wall thereof with an exit adjacent the end of said tubular means at which said abrasive cutting means is located, and means for supplying fluid through said passage means.

3. A surgical instrument as in claim 1 wherein the shield end of said tubular means adjacent said abrasive cutting means includes a hood portion which extends over a front portion of the abrasive cutting means.

4. A surgical instrument as in claim 3 wherein said hood portion includes means for engaging and holding material from the organ.

5. A surgical instrument as in claim 1 wherein the end of said tubular means shielding the abrasive cutting means terminates on a plane which is substantially transverse to the longitudinal axis of the instrument shaft.

6. A surgical instrument as in claim 1 wherein the end of said tubular means shielding the abrasive cutting means terminates on a plane which is at an angle to the longitudinal axis of the instrument shaft.

7. A surgical instrument as in claim 1 wherein said abrasive cutting means comprises means having an abrasive cutting agent on the outer surface thereof.

8. A surgical instrument as in claim 7 wherein said abrasive cutting means is generally spherical in shape.

9. A surgical instrument as in claim 1 wherein said rotatable shaft includes means producing a force to draw material from the organ toward said abrasive cutting means 10. A surgical instrument as in claim 9 wherein said abrasive cutting means is generally spherical in shape.

11. A surgical instrument as in claim 9 wherein said last named means comprises a flute formed on the shaft along a portion of the length thereof.

12. A surgical instrument as in claim 1 wherein said cutter means is generally cylindrical and includes a plurality of blades with exposed cutting edges.

13. A surgical instrument as in claim 9 wherein said abrasive cutting means is in the shape of a truncated cone with the wider diameter base of the cone attached to said shaft.

14. A surgical instrument as in claim 9 wherein said abrasive cutting means is in the shape of a truncated cone with the narrower diameter top of the cone attached to said shaft.

15. A surgical instrument as in claim 1 wherein said cutter means is in the shape of a cone with the wider diameter base portion attached to said rotatable means, said cone formed with a plurality of exposed blade surfaces.

16. A surgical instrument as in claim 1 wherein said cutter means is in the general shape of a solid paraboloid which is formed with a plurality of exposed blade surfaces.

17. A surgical instrument as in claim 1 wherein said cutter means comprises a body with at least one flute forming a cutting surface at the front and side thereof.

18. A surgical instrument as in claim 3 wherein said hood portion extends from said tubular means over a part of the abrasive cutting means and terminates above the longitudinal axis of the shaft.

19. A surgical instrument as in claim 3 wherein said hood portion extends from said tubular means over a part of the abrasive cutting means, crosses the longitudinal axis of the shaft and terminates below the longitudinal axis.

20. A surgical instrument as in claim 3 wherein said hood portion extends from the tubular means, is generally scoop-shaped and terminates in a narrowed-down end.

* * * * *